United States Patent [19]
Cox et al.

[11] Patent Number: 5,977,291
[45] Date of Patent: Nov. 2, 1999

[54] COPOLYESTERS AND METHODS OF THEIR PRODUCTION

[75] Inventors: Michael Kenneth Cox, Tayside; Timothy Hammond, Cleveland; John Christopher Wood, Durham, all of United Kingdom

[73] Assignee: Monsanto Company, St. Louis, Mo.

[21] Appl. No.: 08/809,946

[22] PCT Filed: Sep. 21, 1995

[86] PCT No.: PCT/GB95/02257

§ 371 Date: Sep. 22, 1997

§ 102(e) Date: Sep. 22, 1997

[87] PCT Pub. No.: WO96/09402

PCT Pub. Date: Mar. 28, 1996

[30] Foreign Application Priority Data

Sep. 22, 1994 [GB] United Kingdom .................. 9419082

[51] Int. Cl.$^6$ ................................................. C08G 64/00
[52] U.S. Cl. ........................... 528/272; 528/176; 528/194
[58] Field of Search .................................. 528/176, 193, 528/194, 271, 272

[56] References Cited

FOREIGN PATENT DOCUMENTS

| 0 052 459 | 5/1982 | European Pat. Off. | ........ C08G 63/06 |
| 0 431 883 | 6/1991 | European Pat. Off. | .......... C12P 7/62 |

*Primary Examiner*—Terressa Mosley
*Attorney, Agent, or Firm*—Gary M. Bond; Arnold, White & Durkee

[57] ABSTRACT

A hydroxycarboxylic acid copolyester of R-stereospecific configuration contains a majority of first repeating units capable of forming a highly crystalline high-melting homopolyester and a minority of second repeating units capable when randomly copolycondensed with said first repeating units of lowering the melting point of said homopolyester and is characterised by one or more of: higher crystalline melting point, shorter crystallising time, higher notched impact strength at age 1 month, as compared with corresponding random polyester, and said majority repeating units in the polyester chain being present in blocks longer than correspond to their over-all molar proportionality. The copolyester may be made by fermentation, controlling the distribution of repeating units by reference to the pattern of feeding substrates corresponding to the respective repeating units.

14 Claims, No Drawings

COPOLYESTERS AND METHODS OF THEIR PRODUCTION

THIS INVENTION relates to copolyesters and in particular to those having hydroxy acid repeating units.

Polycondensed hydroxyacids, especially those of R-stereospecific configuration made microbiologically, have recently become commercially available. Of these, poly-3-hydroxybutyric acid homopolymer (PHB) is capable of a high level of crystallinity, but melts at the relatively high temperature 174–180° C., at which loss of molecular weight is relatively rapid. Copolymers (PHBV) containing 3-hydroxyvalerate units at eg 3–30 mol percent melt at a lower temperature and are correspondingly more stable during melt-processing, but they crystallise more slowly.

We have now found that the crystallisation behaviour can be influenced favourably by bringing the repeating units together in a special configuration.

ACCORDING TO THE INVENTION a hydroxycarboxylic acid copolyester of R-stereospecific configuration contains a majority of first repeating units capable of forming a highly crystalline high-melting homopolyester and a minority of second repeating units capable when randomly copolycondensed with said first repeating units of lowering the melting point of said homopolyester:

characterised by one or more of the following features:

a a crystalline melting point higher by at least 10, especially by at least 15° C., than that of the corresponding random copolyester;

b a half-crystallising time at 70° C. or 120° C. less than 0.9, especially less than 0.5, of that of the corresponding random copolyester;

c IZOD 1 mm notched impact strength at age 1 month at least equal to that of the corresponding random polyester of 20% higher molecular weight;

d said majority repeating units in the polyester chain present in blocks longer than correspond to their overall molar proportionality.

The repeating units in the copolyesters preferably include the residues of 3-hydroxybutyric acid (HB) and other hydroxy acids especially 4-hydroxybutyric acid (4HB) or 3-hydroxyvaleric acid (HV). Preferably HB units are in a majority, especially at least 70, especially at least 80, for example 70–98 mol percent of the total units. If desired, the minority units may be of more than one chemical formula. Polyesters containing HB and HV units are referred to hereinafter as "PHBV".

The molecular weight of the polyesters is typically in the range 100000 to 2000000, conveniently 150000 to 1000000. It appears that acceptable mechanical properties are obtainable at molecular weights lower than have been necessary when using random copolyesters of a similar over-all chemical composition.

The invention provides also processes for making the copolymers particularly by fermentation, characterised by controlling the distribution of repeating units by reference to the pattern of feeding substrates corresponding to the respective repeating units, In such a process the following procedures are used:

preferably fed batch operation;

alternating introduction of substrates corresponding to the respective repeating units. Generally a predetermined fraction of the intended consumption of each substrate is fed over a period of time and then withheld until its concentration in the medium is about zero; that is, has fallen to a level between 1% of its maximum fed concentration and the level at which the organism has begun to net-consume its store of polyester. The changeover point may be the same or different for the respective feedstocks. The first feedstock fed may be the majority feedstock or the minority feedstock. The materials actually fed may be chemically 100% of one feedstock or may be a mixture of chemical compounds all producing the same repeating unit, or may be a mixture preponderantly producing one repeating unit but with a small proportion—for example 0.01 to 1.0% w/w producing another. The feed times of each feedstock can be for example in the range 0.5 to 20 h, depending on how great a departure from randomness is required.

preferably a polyester lay-down stage in which a nutrient essential for cell growth is limited; the limiting nutrient is preferably phosphorus, rather than nitrogen but is fed at a concentration permitting a moderate cell growth during polyester lay-down;

preferably medium-soluble nitrogen present; this also appears to provide for the moderate cell growth.

The microorganism used in the fermentation may be any capable of laying down a crystallisable copolyester. When the copolyester is PHBV with PHB in the molar majority, the organism is suitably a bacterium of the genera Alcaliaenes, Athiorhodium, Azotobacter, Bacillus, Nocardia, Pseudomonas, Rhizobium or Spirillium. It may be genetically modified, or the required genetic material may have been grafted into a foreign organism such as a eukariote. Particularly preferred microorganisms are selected from *Alcaliaenes eutrothus* and *Alcaliaenes latus*. Organisms lacking metabolic pathways to produce PHB from feedstocks of odd carbon numbers are especially preferred, since these produce purer PHV in the PHV phase of the fermentation: an example is the modified *A. eutrophus* NCIMB 40124 described in our EP-A-0431883.

The feedstocks in making PHBV copolyesters may be for example:

for HB units: hexoses such as glucose, fructose, gluconate; alcohols and carboxylates having a linear even number of carbon atoms, for example ethanol, acetate and n-butyrate;

for HV units: alcohols and carboxylates having a linear odd number of carbon atoms, for example n-propanol and propionate.

The copolyester can be recovered from the fermentation biomass by known methods, for example solvent extraction or by harvesting, that is, decomposition of non-copolyester cell material. Such decomposition is described in our EP-A-0145233 and more recent patent applications. The polyester product can be in the form of dry solid particles or an aqueous latex. As a result of faster crystallisation, polyesters according to the invention can be harvested as dry solid more easily than corresponding random polyesters, especially those rich in HV, for example over 12 mol percent.

The invention makes it possible to provide polyesters having the same raw chemical composition but a range of mechanical properties, a great increase in convenience compared with changing the feeds to the fermenter and maintaining an inventory of different polyesters for blending.

The polyesters are suitable for use in known shaping procedures and for making articles for which random PHAs are used or proposed. Since they are capable of relatively fast crystallisation they are especially suitable for melt shaping procedures such as extrusion, injection moulding and compression moulding, in which an article is formed in its final shape without mechanical treatment to increase crystallinity substantially. They may be used in processes such as fibre spinning, film extrusion and film casting, and also in such processes, including injection blow moulding with one or more steps of stretching to increase crystallinity towards the maximum attainable. Their faster crystallisation permits shorter cycle times than are at present convenient. The invention polyesters appear to undergo less secondary crystallisation after shaping then do the known random polyesters and thus are less subject to change in mechanical properties after shaping.

The polyesters can be used in solution processing, using for example chloroform, dichloromethane or 1,2-dichloroethane as solvent. If recovered from microbiological cells as latex, or converted to latex by emulsifying a solution and removing the solvent, they can be used in the generality of latex applications, especially coated or bonded products for example coated or bonded paper or cellulose or as a paint component.

In these use operations the polyesters can be formulated, as appropriate with usual processing additives such as pigments, fillers, fibres and plasticisers.

EXAMPLE 1

The following preparation was carried out three times: An aqueous medium containing the following, expressed in g per 1, and having a pH of about 7 (controlled by ammonia addition) was prepared:

| | |
|---|---|
| $MgSO_4.7H_2O$ | 2.2 |
| $K_2SO_4$ | 3.0 |
| $Na_2SO_4$ | 0.18 |
| $FeNH_4$ citrate | 0.17 |
| Glucose | 60 (corrected error) |
| Trace ($SO_4$: Cu 4.5mg, Zn 90mg, Mn 40mg; | |
| Ca acetate 360mg) | |
| Phosphoric acid | 1.69 (ml of 16M). |

A fermenter containing 3 litres of the above medium was inoculated with a starter culture of Alcaligenes eutrophus detailed below. The medium was incubated at 34° C. for 24h until the phosphate content of the medium became limiting.

Each medium was used to produce PHBV from feedstock totalling 400g of carbon (as C) per g of phosphorus (as P) present. The organisms and feedstocks to the three batches were as follows:

A (control): NCIMB 12080 as a variant deposited under the reference NCIMB 40529; glucose (80% of total carbon) and propionic acid (20% of total carbon), fed over 48h at rates giving near-maximal production speed;

B NCIMB 40124 (see our EP-A-0431883); glucose (60% of total carbon) initially 56g over 1 h; then propionic acid (40% of total carbon) 19g over 1 h; then this hourly cycle repeated to 62 h, varying feed rates to give near-maximal production speed;

C NCIMB 40124; glucose and propionic acid in the same over-all carbon proportion as in B; propionic acid below toxic limit for 7 h; glucose for 13 h; propionic acid below toxic limit for 13 h; glucose for 11 h.

In each run the medium was agitated and air-sparged at a rate avoiding oxygen-limitation and build-up of unreacted feedstock. The resulting cells were harvested by heating, treating with protease, oxidising with hydrogen peroxide and separating polyester by centrifuging. The dry cell weight in the batches was:

A: 150 g/l (70% w/w PHBV);
B: 108 g/l (62% w/w PHBV);
C: 128 g/l (62% w/w PHBV).

The polyester products were:

A: 88 mol percent HB, 12 mol percent HV; (This is a substantially random copolyester).

B: 88 mol percent HB, 12 mol percent HV; (The repeating units in this copolyester are believed to be present in short blocks consisting of or preponderating in HB or HV).

C: 88 mol percent HB, 12 mol percent HV. (The repeating units in this copolyester are believed to be present in blocks each longer than in B).

TEST METHODS
MECHANICAL TESTS

Polyester samples were powder blended with 1 phr of boron nitride nucleant and melt processed in a Betol single screw extruder through a 5 mm circular die and granulated to chips. These were injection moulded into test bars. Tensile bars were of gauge length 40 mm with typical cross-sectional areas 2.4×5.3 mm. and were tested on an Instron 1122 instrument fitted with a NENE data analysis program. A crosshead speed of 10 mm per min was used. Izod impact strength was determined using a Zwick pendulum apparatus.

THERMAL ANALYSIS: for Differential Thermal Analysis (DSC) a Mettler TA 4000 instrument was operated under programmed heating control from 20 to 200° C. at 20° C. per min to measure melting behaviour. Tg was measured by this sequence : heating from 20 to 200° C. at 100° C. per min; quenching the molten material to −45° C. by cooling at 100° C. per min; reheating the amorphous sample to 100° C. at 20° C. per min. Tg was the point of inflexion in the heating trace. Crystallisation half times were measured by DSC: A 10 mg sample was melted by heating to 200° C at 20° C per min; held at 2000C. for 2 min; rapidly cooled at 100° C. per min to crystallisation temperature 70° C. (non-nucleated) or 120° C. (nucleated); held isothermally at that temperature for up to 1 h and the crystallisation exotherm recorded. The half time was taken to be the minimum of the crystallisation peak.

TABLE 1

| Polyester | A | B | C |
|---|---|---|---|
| Blocks | Random | Short | Long |
| Property (fresh) | | | |
| Mol percent HV | 12 | 12 | 12 |
| MW moulding '000 | 435 | 299 | 338 |
| Tm ° C. | 156.8 | 169.8 | 172.7 |
| Δ Hm J/g | 60.6 | 45.2 | 54.7 |
| Tc ° C. | do not crystallise on cooling | | |
| Cryst $t_{0.5}$, min at 70° C. | 5.83 | 4.25 | 2.5 |
| Cryst $t_{0.5}$, min at 120° C. | 6.27 | 5.73 | 2.07 |
| Tg ° C. | −0.1 | −1.6 | −0.5 |
| Property (1 month after moulding) | | | |
| Young's modulus MPa | 1027 | 675 | 1049 |
| Stress at peak load MPa | 29 | 22.4 | 29.4 |
| Elongation to break % | 11 | 10.7 | 11.1 |
| 1mm notched IZOD impact J/m | 85 | 113 | 79 |

It is evident that:

Melting points of B and C are substantially higher than for C and indeed approach that of PHB homopolyester (179° C.);

Heat of melting is substantially less and may indicate less total crystallinity, especially for B; Crystallisation is faster, especially for C; At 1 month after moulding, B is noticeably more flexible than the control;

At 1 month the impact strength of B is substantially greater than would be expected in view of its lower molecular weight than A.

EXAMPLE 2

The procedure of runs B and C of Example 1 was repeated with the modifications that the substrate ratio was adjusted to produce 7 or 8 mol percent HV units and the feed times in the long period runs were 12 h instead of 13 h. The products of these runs (D,E) were moulded as described above and tested one month after moulding in comparison with a random copolymer (F) and a blend (G) of PHB homopolymer with an 85:15 B:V copolymer to give a mean V content of 8 mol percent. Results are shown in Table 2.

TABLE 2

| Polyester | D | E | F | G |
|---|---|---|---|---|
| Blocks | Short | Long | Random | Blend |
| Mol percent HV | 7 | 8 | 8 | 8 |
| MW moulding '000 | 554 | 371 | 418 | 429 |
| Tm ° C. | 155.5 | 159.2 | 148.8 | 172.9 |
| $t_{0.5}$, min at 120° C. | 5.7 | 3.3 | 10.0 | 1.6 |
| Young's modulus MPa | 1160 | 1137 | 1241 | 1139 |
| Stress at peak load MPa | 31.46 | 30.18 | 32.27 | 30.61 |
| Elongation to break % | 14.74 | 9.37 | 7.32 | 8.37 |
| 1mm notched IZOD impact J/m | 86.25 | 96.25 | 55.75 | 62.25 |

A useful increase in IZOD impact strength was achieved, with clear improvement in elongation to break, as compared with random or blended polyester.

Note: the microorganisms referred to herein by NCIMB numbers have been deposited with the National Collections of Industrial and Marine Bacteria Limited (NCIMB), POo Box 31, 135 Abbey Road, Aberdeen AB9 8DG, United Kingdom under the terms and conditions of the Budapest Treaty.

94KHC08S-MS-Sep. 19, 1995

We claim:

1. A hydroxycarboxylic acid copolyester of R-stereospecific configuration which contains a majority of first repeating units capable of forming a highly crystalline high-melting homopolyester and a minority of second repeating units capable when randomly copolycondensed with said first repeating units of lowering the melting point of said homopolyester:

characterised by one or more of the following features:

a a crystalline melting point higher by at least 10, especially by at least 15° C., than that of the corresponding random copolyester;

b a half-crystallising time at 70° C. or 120° C. less than 0.9, especially less than 0.5, of that of the corresponding random copolyester;

c IZOD 1 mm notched impact strength at age 1 month at least equal to that of the corresponding random polyester of 20% higher molecular weight;

d said majority repeating units in the polyester chain present in blocks longer than correspond to their over-all molar proportionality.

2. A copolyester according to claim 1 in which the repeating units in the copolyesters include the residues of 3-hydroxybutyric acid (HB) and other hydroxy acids especially 4-hydroxybutyric acid (4HB) or 3-hydroxyvaleric acid (HV).

3. A copolyester according to claim 2 in which HB units are at least 70 mol percent of the total units.

4. A process for making a copolyester of claim 1 by fermentation organism characterised by controlling the distribution of repeating units by reference to the pattern of feeding substrates corresponding to the respective repeating units.

5. A process according to claim 4 operated on a fed batch basis with alternating introduction of substrates corresponding to the respective repeating units, a predetermined fraction of the intended consumption of each substrate being fed over a period of time and then withheld until its concentration has fallen to a level between 1% of its maximum fed concentration and the level at which the organisms has begun to net-consume its store of polyester.

6. A process according to claim 4 including a polyester lay-down stage in which a nutrient essential for cell growth is limited, characterised in that the limiting nutrient is phosphorus but is fed at a concentration permitting a moderate extent of cell growth accompanying said polyester lay-down.

7. A process according to claim 4 in which the fermentation organism lacks metabolic pathways to produce HB units from substrates of odd carbon numbers.

8. A process according to any one of claim 4 in which fermentation organism is Alcaliaenes eutrophus.

9. A process according to any one of the preceding claims including recovery of copolyester from fermentation biomass by decomposition of non-copolyester cell material.

10. A process according to claim 9 in which the copolyester is recovered as dry solid particles.

11. A process of making shaped articles by melt-shaping a polyester according to any one of claims 1 to 3 or made a process according to any one of claims 4 to 10.

12. A process according to claim 11 in which the article formed in its final shape without mechanical treatment increase its crystallinity substantially.

13. A process according to claim 9 in which the polyester is recovered as a latex.

14. A process of making coated and/or bonded products by application of a latex of a copolyester according to any of claims 1 to 3 or as made by a process according to one of claims 4 to 9 and 13.

* * * * *

UNITED STATES PATENT AND TRADEMARK OFFICE
CERTIFICATE OF CORRECTION

PATENT NO. : 5,977,291

DATED : November 2, 1999

INVENTOR(S) : Michael Kenneth Cox, Timothy Hammond, and John Christopher Wood

It is certified that error appears in the above-identified patent and that said Letters Patent is hereby corrected as shown below:

In column 6, line 34, please delete the phrase "any one of".

In column 6, line 35, please delete "Alcaliaenes" and substitute therefor --Alcaligenes--.

In column 6, line 36, please delete the phrase "any one of the preceding claims" and replace it with --claim 4--.

In column 6, line 45, after the word "treatment", please insert "to".

Signed and Sealed this

Sixteenth Day of May, 2000

*Attest:*

Q. TODD DICKINSON

*Attesting Officer*      *Director of Patents and Trademarks*